US012758757B2

(12) United States Patent
Ma

(10) Patent No.: US 12,758,757 B2
(45) Date of Patent: Oct. 13, 2026

(54) CAP FOR A PORT OF AN INTRAVENOUS DEVICE

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 869 days.

(21) Appl. No.: 18/094,796

(22) Filed: Jan. 9, 2023

(65) Prior Publication Data

US 2023/0233829 A1 Jul. 27, 2023

Related U.S. Application Data

(60) Provisional application No. 63/302,918, filed on Jan. 25, 2022.

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01)

(58) Field of Classification Search
CPC .................................................. A61M 39/162
See application file for complete search history.

(56) References Cited

U.S. PATENT DOCUMENTS

| | | | | |
|---|---|---|---|---|
| 2009/0008393 | A1 | 1/2009 | Howlett et al. | |
| 2012/0022469 | A1 * | 1/2012 | Alpert .................. | A61M 39/16 604/533 |
| 2013/0184679 | A1 * | 7/2013 | Ziebol .................. | A61M 1/169 604/533 |
| 2019/0351212 | A1 | 11/2019 | Dudar et al. | |
| 2020/0269033 | A1 | 8/2020 | Corrigan et al. | |
| 2021/0205596 | A1 | 7/2021 | Ziebol et al. | |

* cited by examiner

*Primary Examiner* — Bradley J Osinski
(74) *Attorney, Agent, or Firm* — Kirton McConkie; Whitney Blair; Kevin Stinger

(57) ABSTRACT

A cap for a port of an intravenous device may include a solid post configured to insert into a port of an intravenous device. The cap may include an annular collar surrounding the solid post, and an annular cavity disposed between the solid post and the annular collar. The cap may include an absorbent material containing an antimicrobial solution. The absorbent material may be disposed within the annular cavity such that the absorbent material is compressible. In response to the cap being connected to the port of the intravenous device, the absorbent material may be configured to be compressed causing the antimicrobial solution to flow onto the port of the intravenous device.

13 Claims, 7 Drawing Sheets

CAP FOR A PORT OF AN INTRAVENOUS DEVICE

RELATED APPLICATIONS

This application claims the benefit of U.S. Provisional Patent Application No. 63/302,918, filed Jan. 25, 2022, and entitled CAP FOR A PORT OF AN INTRAVENOUS DEVICE, which is incorporated herein in its entirety.

BACKGROUND

Intravenous devices can employ ports to provide quick access to a patient's vasculature. These ports also enable the intravenous devices to remain within the patient's vasculature even when no access to the vasculature is needed. When a port of an intravenous device is not in use, it is desirable to maintain the port clean and free from bacteria and other microbes. If the port becomes contaminated with microbes while not in use, it is possible that the microbes will be flushed into the patient's vasculature once the port is again used for accessing the patient's vasculature. Accordingly, maintaining sterility of the port is essential to reduce a risk of infection.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a cap for a port of an intravenous device, as well as related devices and methods. In some embodiments, the present disclosure relates to a cap that provides both intraluminal and extraluminal antimicrobial protection. In some embodiments, the cap may include an antimicrobial solution for extraluminal protection and an antimicrobial coating for intraluminal protection. In some embodiments, the cap for the port of the intravenous device may include a solid post configured to insert into a port of an intravenous device. In some embodiments, the cap may include an annular collar surrounding the solid post. In some embodiments, the solid post may be tapered inwardly. In some embodiments, the solid post may extend further distally than the annular collar.

In some embodiments, the cap may include an annular cavity disposed between the solid post and the annular collar. In some embodiments, the cap may include an absorbent material containing the antimicrobial solution. In some embodiments, the absorbent material may be disposed within the annular cavity such that the absorbent material is compressible. In some embodiments, in response to the cap being connected to the port of the intravenous device, the absorbent material may be configured to be compressed causing the antimicrobial solution to flow onto the port of the intravenous device.

In some embodiments, the cap may include the antimicrobial coating disposed on a distalmost surface of the solid post. In some embodiments, the solid post may include an annular stepped surface, a proximal portion proximate and proximal to the annular stepped surface, and a distal portion proximate and distal to the annular stepped surface. In some embodiments, an outer circumference of the distal portion may be less than an outer circumference of the proximal portion. In some embodiments, the antimicrobial coating may be disposed on the distal portion and surround the distal portion. In some embodiments, the antimicrobial coating may be flush with the proximal portion.

In some embodiments, the annular stepped surface may be disposed within the annular collar. In some embodiments, the annular stepped surface may be disposed distal to the annular collar. In some embodiments, the antimicrobial coating disposed on the distal portion may include an outer diameter less than an outer diameter of the proximal portion. In some embodiments, the antimicrobial coating may cover an entirety of the distalmost surface and is flush with a distal end of the solid post.

In some embodiments, a lid portion may be disposed at a proximal end of the cap. In some embodiments, the annular collar and the solid post may extend from the lid portion. In some embodiments, the lid portion may include a circular disc and close the annular cavity. In some embodiments, the cap may include a cover coupled to the annular collar and covering the antimicrobial coating.

In some embodiments, an intravenous device may include the port and the cap coupled to the port. In some embodiments, the cap may include a solid post configured to insert into the port. In some embodiments, the cap may include the annular collar surrounding the solid post, and the annular cavity disposed between the solid post and the annular collar. In some embodiments, the cap may include the absorbent material containing the antimicrobial solution. In some embodiments, the absorbent material may be disposed within the annular cavity such that the absorbent material is compressible. In some embodiments, in response to the cap being connected to the port, the absorbent material may be configured to be compressed causing the antimicrobial solution to flow onto the port.

In some embodiments, the port may include a septum. In some embodiments, in response to the cap being connected to the port, the septum may contact the absorbent material to compress the absorbent material causing the antimicrobial solution to flow onto the septum. In some embodiments, in response to the cap being connected to the port, the septum may contact the absorbent material to compress the absorbent material causing the antimicrobial solution to flow onto the septum and an outer surface of the port.

In some embodiments, the cap may include the antimicrobial coating disposed on a distalmost surface of the solid post. In some embodiments, the intravenous device may include a connector. In some embodiments, a proximal end of the connector may include the port. In some embodiments, the connector may include a cavity distal to the port. In some embodiments, the antimicrobial coating may be disposed within the cavity.

In some embodiments, the solid post may include the annular stepped surface, the proximal portion proximate and proximal to the annular stepped surface, and the distal portion proximate and distal to the annular stepped surface. In some embodiments, the outer circumference of the distal portion may be less than the outer circumference of the proximal portion. In some embodiments, the antimicrobial coating may be disposed on the distal portion and surround the distal portion. In some embodiments, the antimicrobial coating may be flush with the proximal portion. In some embodiments, the annular stepped surface may be disposed distal to the annular collar.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1B:
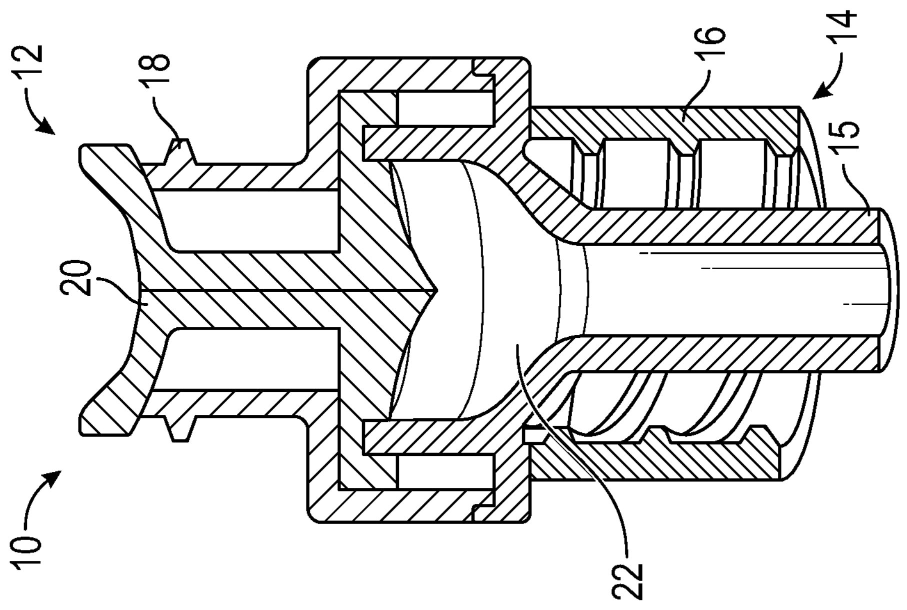
FIG. 1B is a cross-sectional view of an example connector of the intravenous device.
Figure 1A:
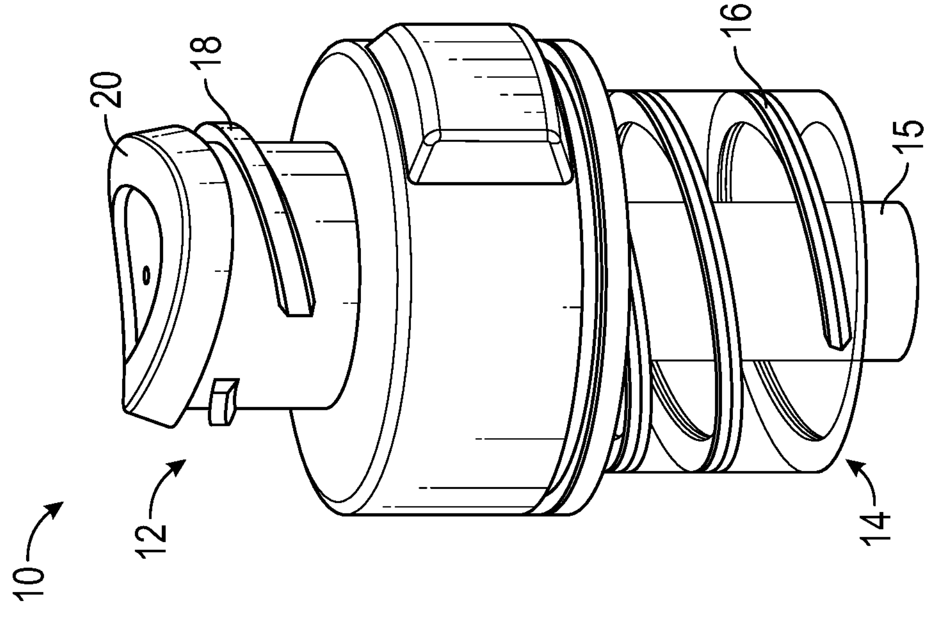
FIG. 1A is an upper perspective view of an example connector of an intravenous device.

Referring now to FIGS. 1A-1B, in some embodiments, a connector 10 of an intravenous device may include a proximal end 12 and a distal end 14. As used in the present disclosure, the term "distal" refers to a portion that is described which is further from a user, while the term "proximal" refers to a portion that is being described which is closer to the user. FIGS. 1A-1B illustrate an example of the connector 10. However, it is understood that in some embodiments, the connector 10 may include any suitable needle-free connector of an intravenous device. In some embodiments, the distal end 14 may include a male luer 15 and/or a collar 16 surrounding the male luer 15. In some embodiments, the proximal end 12 may include a port 18, which may be threaded. In some instances, the port 18 may include a female luer.

In some embodiments, the port 18 may include a septum 20 extending therethrough and sealing an interior of the connector 10 from an exterior environment. In some embodiments, a lumen 21 of the connector 10 extending through the proximal end 12 and the distal end 14 may include a cavity 22 distal to the port 18. In some embodiments, the cavity 22 may be wider than the male luer 15. In some embodiments, the intravenous device may include a catheter assembly, which may be coupled to the connector 10.

Figure 2C:
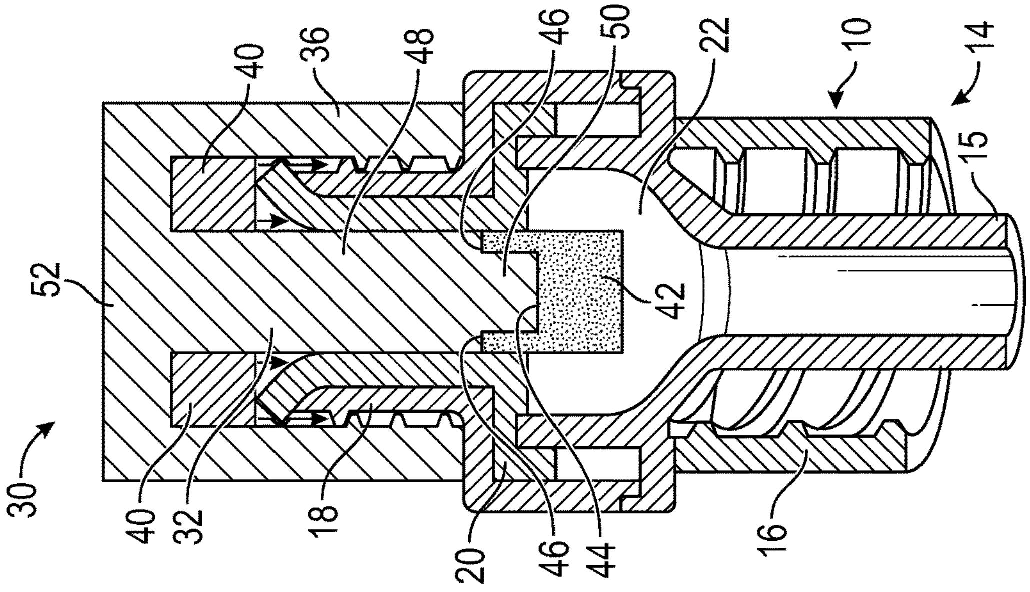
FIG. 2C is a cross-sectional view of the cap of FIG. 2A coupled to the connector, according to some embodiments.
Figure 2B:
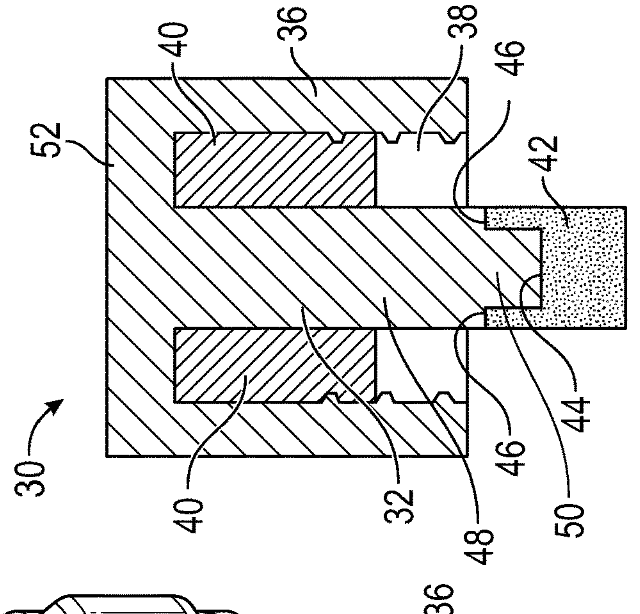
FIG. 2B is a cross-sectional view of the cap of FIG. 2A, according to some embodiments.
Figure 2A:
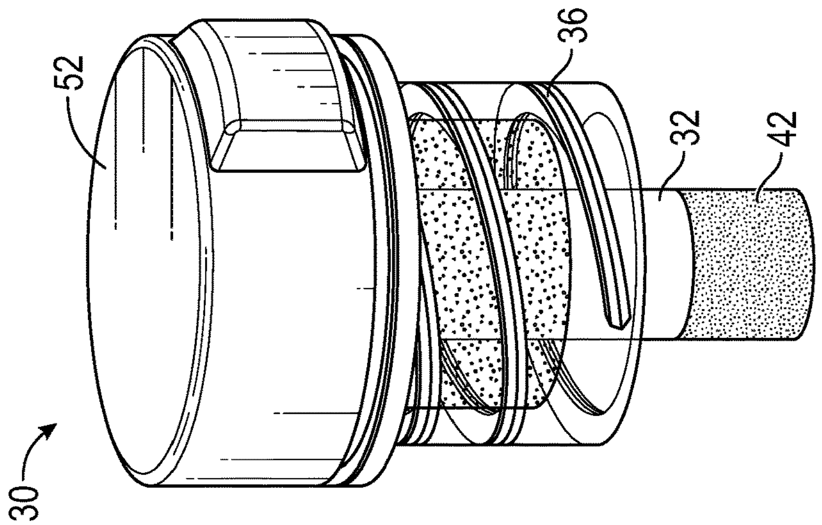
FIG. 2A is an upper perspective view of an example cap, according to some embodiments.

Referring now to FIGS. 2A-2C, in some embodiments, a cap 30 for the port 18 of the intravenous device, or another similar port, may include a solid post 32 configured to insert into the port 18. In some embodiments, the cap 30 may include an annular collar 36 surrounding the solid post 32. In some embodiments, the annular collar 36 may include threads such that the annular collar 36 is configured to be threaded to the port 18. In some embodiments, the annular collar 36 may not include the threads and may be configured to be slip fit with the port 18.

In some embodiments, the cap 30 may include an annular cavity 38 disposed between the solid post 32 and the annular collar 36. In some embodiments, the cap 30 may include an absorbent material 40 containing an antimicrobial solution. In some embodiments, the antimicrobial solution may include chlorhexidine gluconate (CHG), alcohol, or another suitable antimicrobial solution. In some embodiments, the absorbent material 40 may be disposed within the annular cavity 38 such that the absorbent material 40 is compressible. In some embodiments, the absorbent material 40 may be annular. FIG. 2B illustrates the absorbent material 40 uncompressed, according to some embodiments. FIG. 2C illustrates the absorbent material 40 compressed when the connector 10 is capped, according to some embodiments.

In some embodiments, in response to the cap 30 being connected to the port 18, the septum 20 or another portion of the connector 10 may contact the absorbent material 40 to compress the absorbent material 40 causing the antimicrobial solution to flow onto the septum 20. In some embodiments, only the septum 20 of the connector 10 may contact the absorbent material 40 to compress the absorbent material 40. In some embodiments, the antimicrobial solution may flow onto an extraluminal portion of the septum 20 outside of the lumen 21, providing antimicrobial protection. In some embodiments, in response to the cap 30 being connected to the port 18, the septum 20 may contact the absorbent material 40 to compress the absorbent material 40 causing the antimicrobial solution to flow onto the septum 20 and/or an outer surface of the port 18. In these and other embodiments, the antimicrobial solution may flow distally through a space between the septum 20 and an inner surface of the port 18 as illustrated, for example, in FIG. 2C.

In some embodiments, the solid post 32 may be tapered inwardly such as an outer surface of a male luer taper. In some embodiments, the solid post 32 may be tapered inwardly in a distal direction along all or a portion of a length of the solid post 32, which may facilitate insertion of the solid post 32 through the septum 20. In these embodiments, the solid post 32 may include a truncated cone shape. In some embodiments, the solid post 32 may be cylindrical.

In some embodiments, the cap 30 may include an antimicrobial coating 42 disposed on a distalmost surface 44 of the solid post 32. In some embodiments, the cap 30 may provide intraluminal and/or extraluminal antimicrobial protection. In some embodiments, the cap 30 may include the antimicrobial solution for extraluminal protection and only the antimicrobial coating 42 for intraluminal protection. In some embodiments, the antimicrobial coating 42 may be configured to elute an antimicrobial agent in response to contact with a catheter lock solution disposed within the lumen 21 and the cavity 22. In some embodiments, the antimicrobial coating 42 may include chlorhexidine acetate (CHA), silver, a combination of CHA and silver, or another suitable antimicrobial coating.

In some embodiments, the solid post 32 that is cylindrical or just slightly tapered may facilitate the distalmost surface 44 being larger to accommodate more antimicrobial coating 42. In some embodiments, the solid post 32 may extend further distally than the annular collar 36, which may facilitate placement of the antimicrobial coating 42 deep within the lumen 21, such as, for example, in the cavity 22. In some embodiments, the distalmost surface 44 may be planar or generally planar.

In some embodiments, the solid post 32 may include an annular stepped surface 46, a proximal portion 48 proximate and proximal to the annular stepped surface 46, and a distal portion 50 proximate and distal to the annular stepped surface 46. In some embodiments, the distal portion may be proximate the distalmost surface 44. In some embodiments, an outer circumference of the distal portion 50 may be less than an outer circumference of the proximal portion 48. In some embodiments, the antimicrobial coating 42 may be disposed on the distal portion 50 and surround the distal portion 50.

In some embodiments, the annular stepped surface 46 may allow the antimicrobial coating 42 to be flush with the proximal portion 48. In these embodiments, the antimicrobial coating 42 may not increase an outer diameter of the solid post 32 and thus may not affect a surface of a cylinder or the male luer taper of the solid post 32. In some embodiments, the antimicrobial coating 42 may maintain a same angle as the distal portion 50. In some embodiments, the annular stepped surface 46 may be disposed distal to the annular collar 36, which may concentrate the antimicrobial coating 42 distally within the lumen 21, where the antimicrobial coating 42 may come into increased contact with the catheter lock solution. In some embodiments, the annular stepped surface 46 may allow the antimicrobial coating 42 to extend annular around the solid post 32, increasing a length of the antimicrobial coating 42 along the solid post 32 while not increasing the outer diameter of the solid post 32.

In some embodiments, a lid portion 52 may be disposed at a proximal end 54 of the cap 30. In some embodiments, the annular collar 36 and the solid post 32 may extend distally from the lid portion 52. In some embodiments, the lid portion 52 may include a circular disc and/or may close the annular cavity 38. In some embodiments, the absorbent material 40 may contact the lid portion 52 and may be configured to be compressed towards the lid portion 52.

Figure 3C:
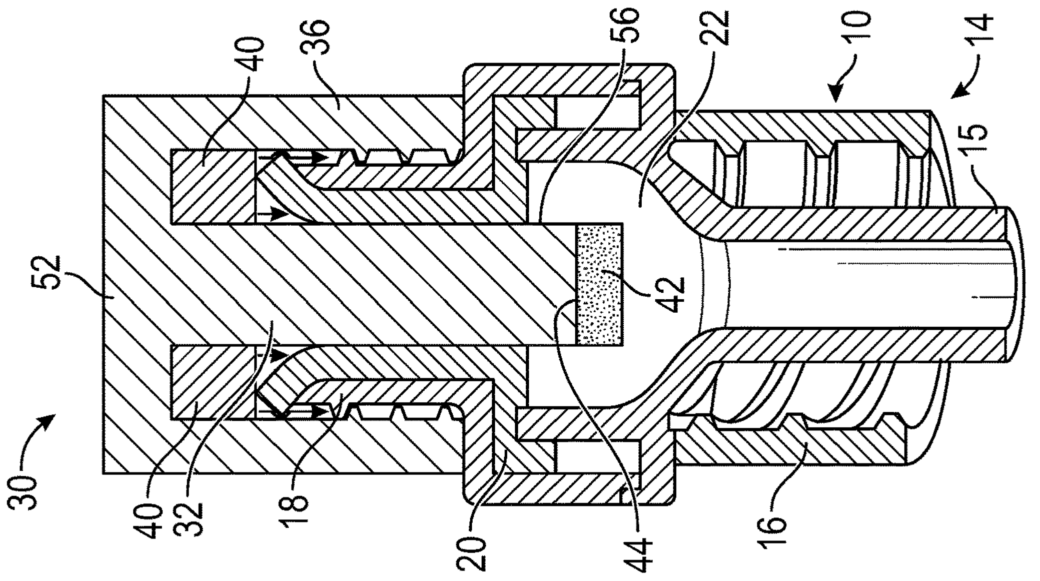
FIG. 3C is a cross-sectional view of the cap of FIG. 3A coupled to the connector, according to some embodiments.
Figure 3B:
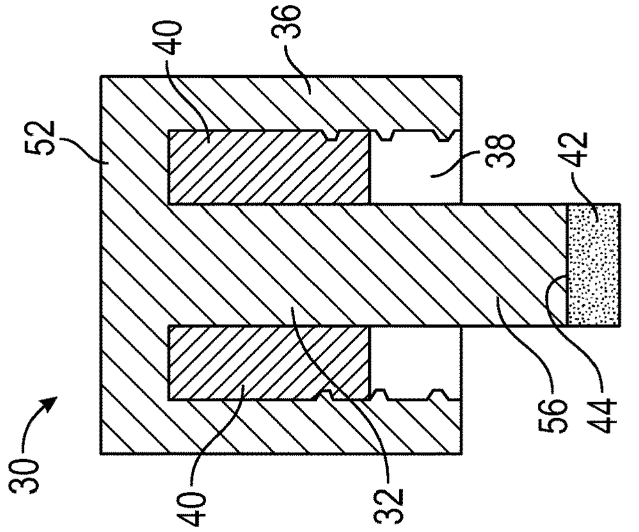
FIG. 3B is a cross-sectional view of the cap of FIG. 3A, according to some embodiments.
Figure 3A:
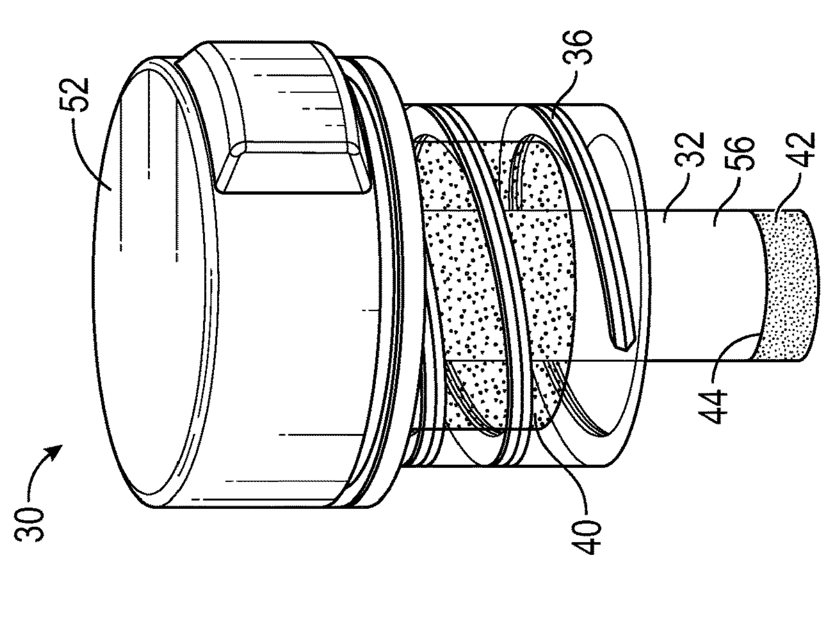
FIG. 3A is an upper perspective view of an example cap, according to some embodiments.

Referring now to FIGS. 3A-3C, in some embodiments, the antimicrobial coating 42 may cover an entirety of the distalmost surface 44 and may be flush with a distal end 56 of the solid post 32. In these embodiments, the antimicrobial coating 42 may not increase an outer diameter of the solid post 32 and thus may not affect a surface of a cylinder or the male luer taper of the solid post 32. In some embodiments, the antimicrobial coating 42 may maintain a same angle as the distal end 56. In some embodiments, the antimicrobial coating 42 covering the entirety of the distalmost surface 44 may increase an amount of antimicrobial coating 42 present in the lumen 21 to provide antimicrobial protection. FIG. 3B illustrates the absorbent material 40 uncompressed, according to some embodiments. FIG. 3C illustrates the absorbent material 40 compressed when the connector 10 is capped, according to some embodiments.

Figure 4C:
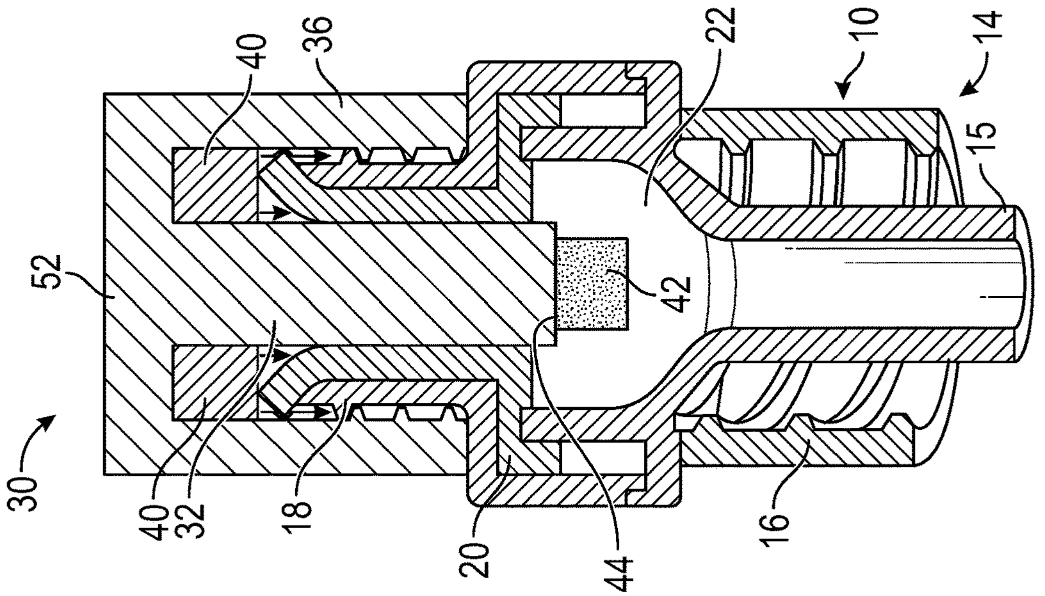
FIG. 4C is a cross-sectional view of the cap of FIG. 4A coupled to the connector, according to some embodiments.
Figure 4B:
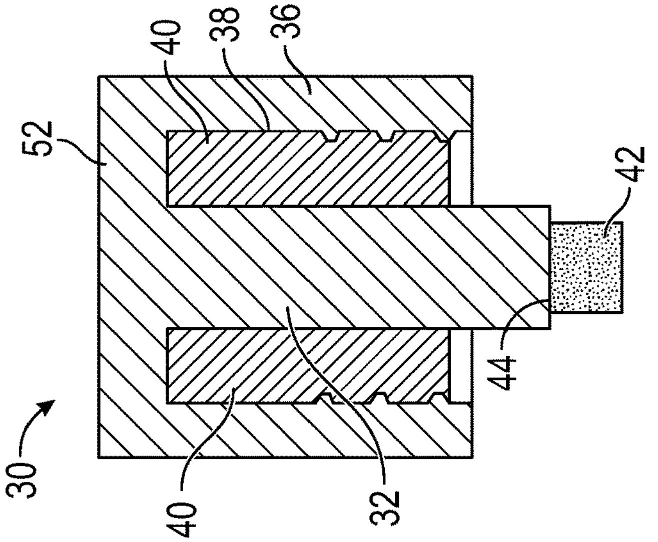
FIG. 4B is a cross-sectional view of the cap of FIG. 4A, according to some embodiments.
Figure 4A:
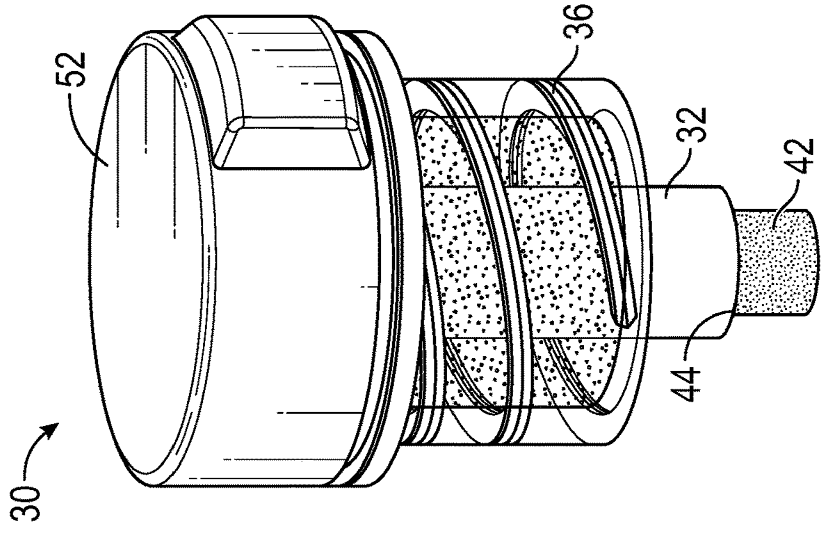
FIG. 4A is an upper perspective view of an example cap, according to some embodiments.

Referring now to FIGS. 4A-4C, in some embodiments, the antimicrobial coating 42 disposed on the distalmost surface 44 may include an outer diameter less than an outer diameter of the distalmost surface 44, creating an annular step between the distalmost surface 44 and the antimicrobial coating 42. In some embodiments, the outer diameter of the antimicrobial coating 42 less than the outer diameter of the distalmost surface 44 may facilitate extension of the antimicrobial coating 42 further into the connector 10, which may be narrower. In some embodiments, the connector 10 may include the cavity 22 distal to the port. FIG. 4B illustrates the absorbent material 40 uncompressed, according to some embodiments. FIG. 4C illustrates the absorbent material 40 compressed when the connector 10 is capped, according to some embodiments.

Figure 5C:
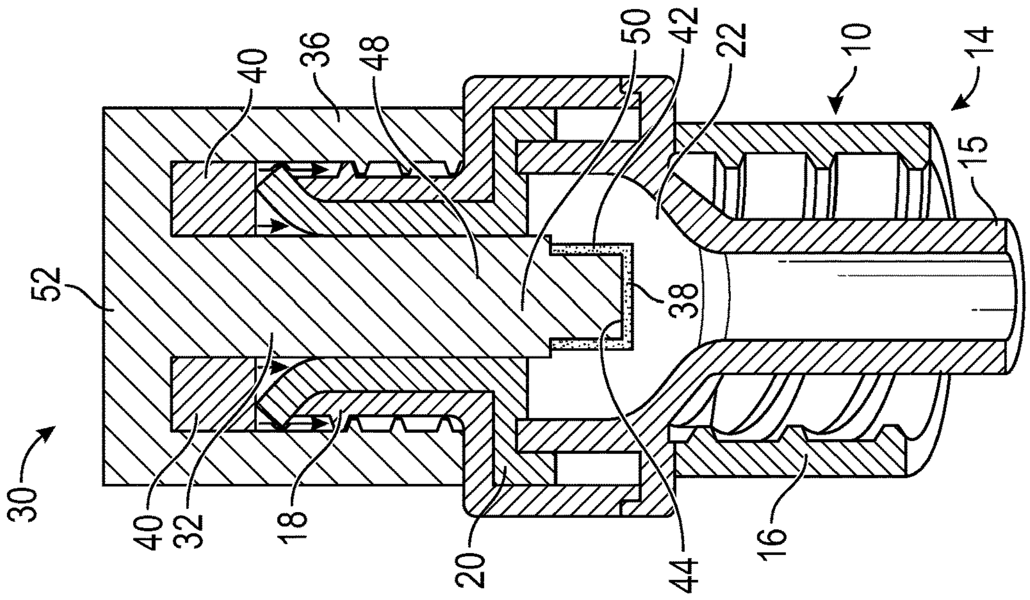
FIG. 5C is a cross-sectional view of the cap of FIG. 5A coupled to the connector, according to some embodiments.
Figure 5B:
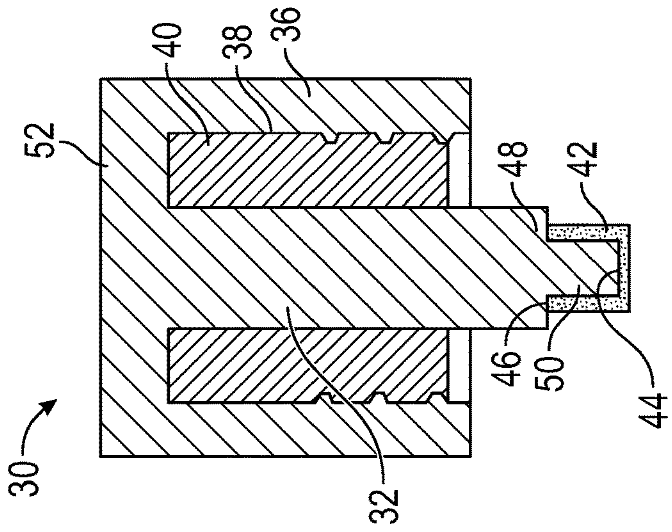
FIG. 5B is a cross-sectional view of the cap of FIG. 5A, according to some embodiments.
Figure 5A:
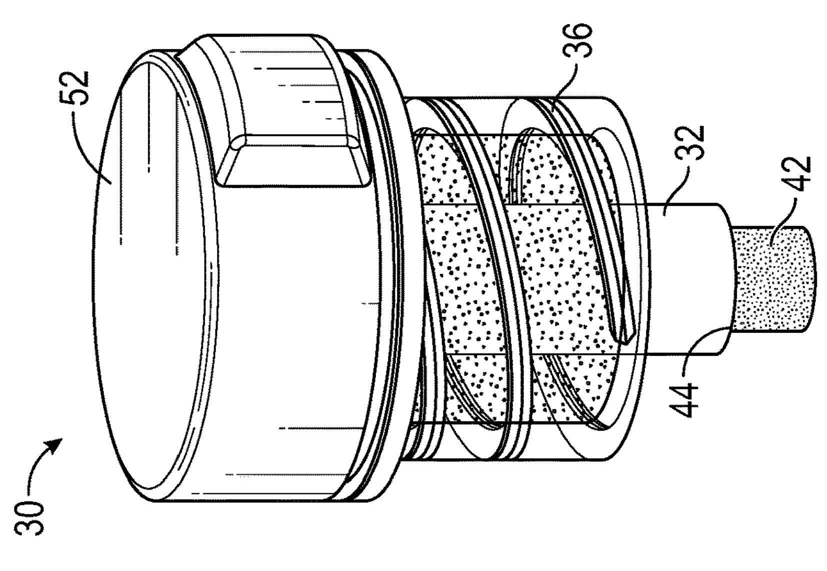
FIG. 5A is an upper perspective view of an example cap, according to some embodiments.

Referring now to FIGS. 5A-5C, in some embodiments, the antimicrobial coating 42 disposed on the distal portion 50 may include an outer diameter less than an outer diameter of the proximal portion 48, creating an annular step between the distal portion 50 and the antimicrobial coating 42. In some embodiments, the outer diameter of the antimicrobial coating 42 less than the outer diameter of the proximal portion 48 may facilitate extension of the antimicrobial coating 42 further into the connector 10, which may be narrower. FIG. 5B illustrates the absorbent material 40 uncompressed, according to some embodiments. FIG. 5C illustrates the absorbent material 40 compressed when the connector 10 is capped, according to some embodiments.

Figure 6C:
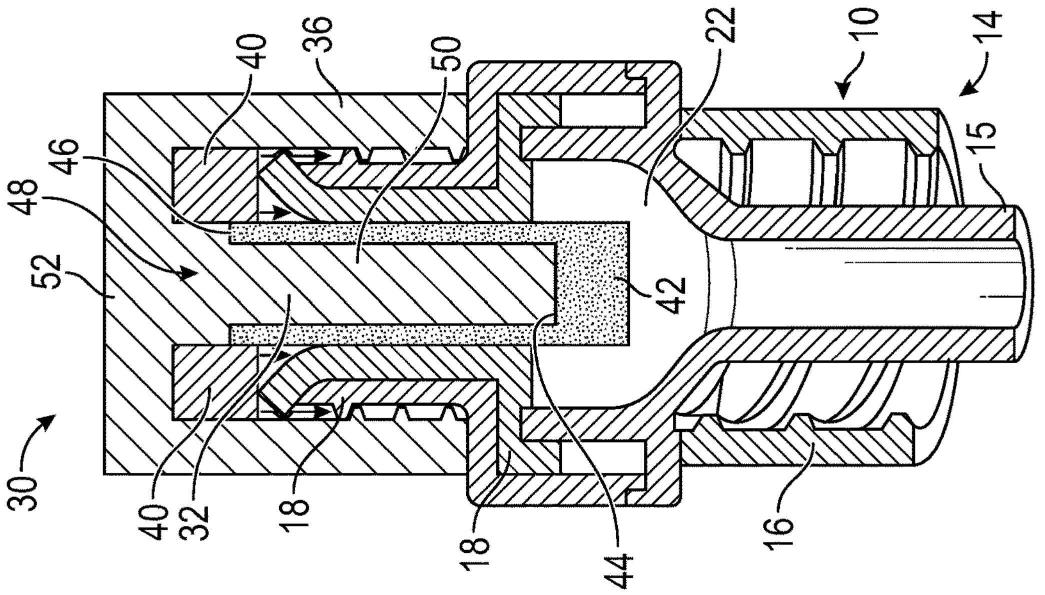
FIG. 6C is a cross-sectional view of the cap of FIG. 6A coupled to the connector, according to some embodiments.
Figure 6B:
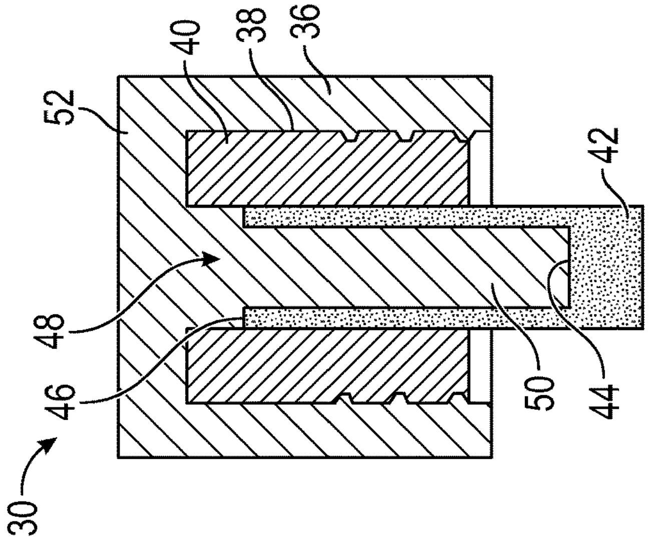
FIG. 6B is a cross-sectional view of the cap of FIG. 6A, according to some embodiments.
Figure 6A:
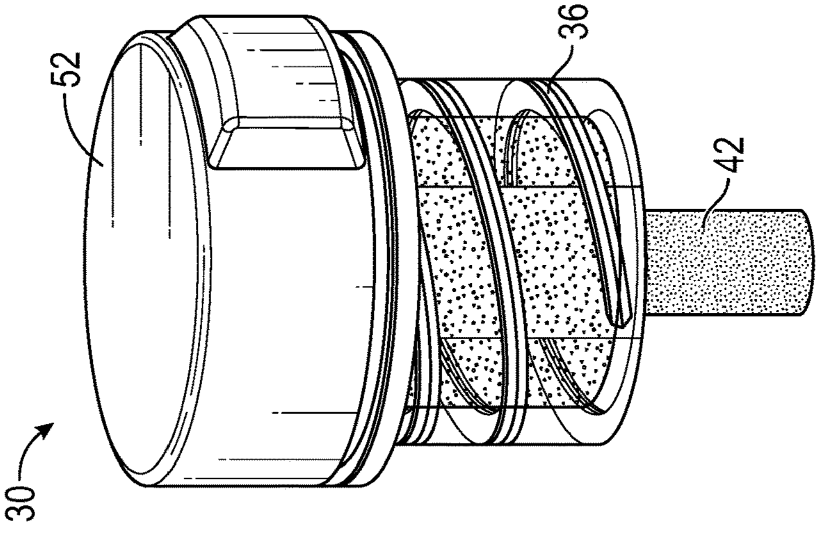
FIG. 6A is an upper perspective view of an example cap, according to some embodiments.

Referring now to FIGS. 6A-6C, in some embodiments, the annular stepped surface 46 may be disposed within the annular collar 36. In these embodiments, the antimicrobial coating 42 may contact the absorbent material 40, which may be soaked with saline solution or ionized water. In some embodiments, in response to the antimicrobial coating 42 contacting the absorbent material 40 after assembly of the cap 30 (such as, for example, during sterilization, transportation, and/or storage), the antimicrobial coating 42 may elute an antimicrobial agent, producing an antimicrobial solution that may then protect extraluminal surfaces of the connector 10 when the connector 10 is capped. FIG. 6B illustrates the absorbent material 40 uncompressed, according to some embodiments. FIG. 6C illustrates the absorbent material 40 compressed when the connector 10 is capped, according to some embodiments.

Figure 7B:
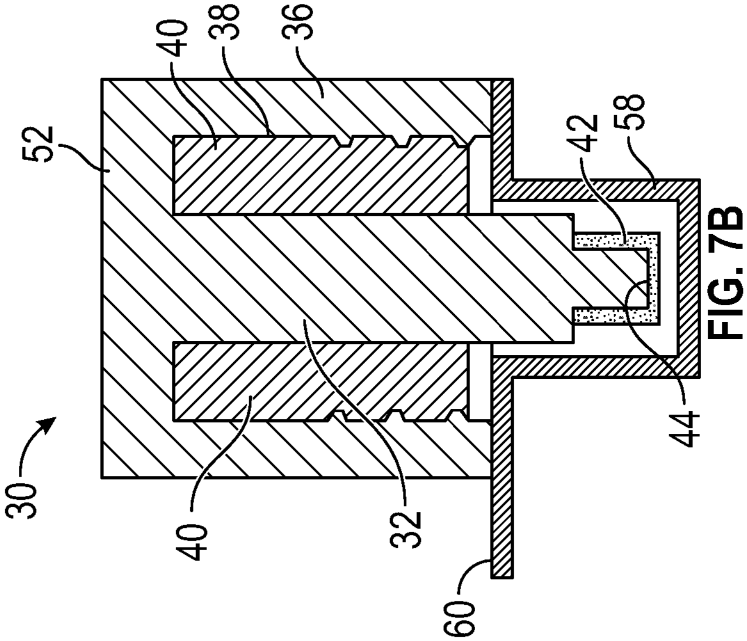
FIG. 7B is a cross-sectional view of the cover on the cap of FIG. 7A, according to some embodiments.
Figure 7A:
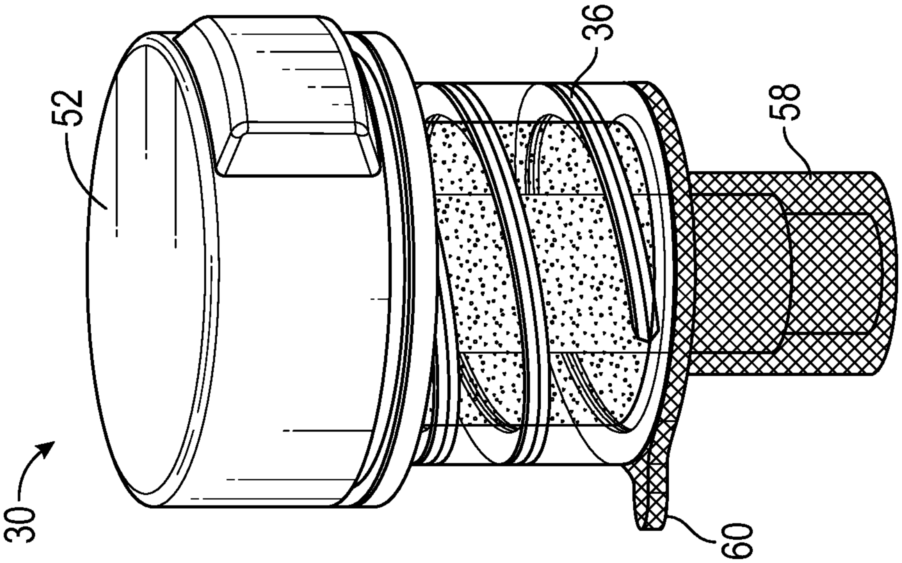
FIG. 7A is an upper perspective view of an example cover disposed on an example cap, according to some embodiments.

Referring now to FIGS. 7A-7B, in some embodiments, the cap 30 may include a cover 58, which may be coupled to the annular collar 36. In some embodiments, the cover 58 may cover the antimicrobial coating 42. In some embodiments, the cover 58 may seal off the cap 30 and prevent evaporation of the antimicrobial solution in the absorbent material 40. In some embodiments, the cover 58 may be attached to a surface of the cap 30, such as the annular collar 36, using pressure sensitive adhesive (PSA), a mechanical snap feature, or another suitable means. In some embodiments, a user may remove the cover 58 from a remaining portion of the cap 30 before coupling the cap 30 to the connector 10 or capping the connector 10. In some embodiments, the cover 58 may include a tab 60, which may facilitate peeling off of the cover 58 by the user. It is understood that the cover 58 may be used with any of the embodiments of the cap 30 of FIGS. 2-6. Moreover, it is understood that one or more of the embodiments of FIGS.

2-6 may be combined such that a particular embodiment may include be similar to one or more other embodiments in terms of one or more components and/or operation.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A cap for a port of an intravenous device, the cap comprising:

a solid post configured to insert into the port of the intravenous device;

an annular collar surrounding the solid post;

an annular cavity disposed between the solid post and the annular collar; and an absorbent material containing an antimicrobial solution, wherein the absorbent material is disposed within the annular cavity such that the absorbent material is compressible, wherein in response to the cap being connected to the port of the intravenous device, the absorbent material is configured to be compressed causing the antimicrobial solution to flow onto the port of the intravenous device; and wherein the solid post comprises an annular stepped surface, a proximal portion proximate and proximal to the annular stepped surface, and a distal portion proximate and distal to the annular stepped surface, wherein an outer circumference of the distal portion is less than an outer circumference of the proximal portion, wherein an antimicrobial coating is disposed on the distal portion and surrounds the distal portion, wherein the antimicrobial coating is flush with the proximal portion.

2. The cap of claim 1, wherein the solid post is tapered inwardly.

3. The cap of claim 1, wherein the solid post extends further distally than the annular collar.

4. The cap of claim 1, wherein the annular stepped surface is disposed within the annular collar.

5. The cap of claim 1, wherein the annular stepped surface is disposed distal to the annular collar.

6. The cap of claim 1, wherein the antimicrobial coating covers an entirety of a distalmost surface of the solid post and is flush with a distal end of the solid post.

7. The cap of claim 1, further comprising a lid portion disposed at a proximal end of the cap, wherein the annular collar and the solid post extend from the lid portion, wherein the lid portion comprises a circular disc and closes the annular cavity.

8. The cap of claim 1, further comprising a cover coupled to the annular collar and covering the antimicrobial coating.

9. The intravenous device of claim 1, wherein the intravenous device comprises a connector, wherein a proximal end of the connector comprises the port, wherein the connector comprises a cavity distal to the port, wherein the antimicrobial coating is disposed within the cavity.

10. The intravenous device of claim 1, wherein the annular stepped surface is disposed distal to the annular collar.

11. An intravenous device, comprising:

a port; and a cap connected to the port, the cap comprising:

a solid post configured to insert into the port;

an annular collar surrounding the solid post;

an annular cavity disposed between the solid post and the annular collar; and an absorbent material containing an antimicrobial solution, the absorbent material disposed within the annular cavity such that the absorbent material is compressible, wherein in response to the cap being connected to the port, the absorbent material is configured to be compressed causing the antimicrobial solution to flow onto the port, wherein the solid post comprises an annular stepped surface, a proximal portion proximate and proximal to the annular stepped surface, and a distal portion proximate and distal to the annular stepped surface, wherein an outer circumference of the distal portion is less than an outer circumference of the proximal portion, wherein an antimicrobial coating is disposed on the distal portion and surrounds the distal portion, wherein the antimicrobial coating is flush with the proximal portion.

12. The intravenous device of claim 11, wherein the port comprises a septum, wherein in response to the cap being connected to the port, the septum contacts the absorbent material to compress the absorbent material causing the antimicrobial solution to flow onto the septum.

13. The intravenous device of claim 12, wherein in response to the cap being connected to the port, the septum contacts the absorbent material to compress the absorbent material causing the antimicrobial solution to flow onto the septum and an outer surface of the port.

* * * * *